(12) United States Patent
Gerrah et al.

(10) Patent No.: US 8,753,365 B2
(45) Date of Patent: Jun. 17, 2014

(54) DEVICE FOR HARVESTING A BLOOD VESSEL

(76) Inventors: Rabin Gerrah, Rego Park, NY (US); Omid David Tabibi, Bat-Yam (IL)

(*) Notice: Subject to any disclaimer, the term of this patent is extended or adjusted under 35 U.S.C. 154(b) by 1043 days.

(21) Appl. No.: 12/667,868

(22) PCT Filed: Jun. 29, 2008

(86) PCT No.: PCT/IL2008/000885
§ 371 (c)(1),
(2), (4) Date: Jan. 5, 2010

(87) PCT Pub. No.: WO2009/004610
PCT Pub. Date: Jan. 8, 2009

(65) Prior Publication Data
US 2010/0198241 A1    Aug. 5, 2010

Related U.S. Application Data

(60) Provisional application No. 60/958,297, filed on Jul. 5, 2007.

(51) Int. Cl.
A61B 17/32    (2006.01)

(52) U.S. Cl.
USPC ............................................. 606/169; 606/190

(58) Field of Classification Search
CPC ............... A61B 17/282; A61B 17/230092; A61B 2017/00252; A61B 2017/2926
USPC .................................. 606/169, 159, 167
See application file for complete search history.

(56) References Cited

U.S. PATENT DOCUMENTS

| 5,511,564 | A  | * | 4/1996  | Wilk ............................. 128/898 |
| 6,558,376 | B2 | * | 5/2003  | Bishop ............................ 606/27 |
| 8,100,824 | B2 | * | 1/2012  | Hegeman et al. .............. 600/141 |
| 2002/0002380 | A1 | * | 1/2002 | Bishop .......................... 606/169 |
| 2005/0010242 | A1 | * | 1/2005 | Lindsay ........................ 606/154 |
| 2006/0173453 | A1 | * | 8/2006 | Gruhl et al. .................... 606/50 |
| 2007/0004984 | A1 | * | 1/2007 | Crum et al. .................... 600/471 |
| 2007/0038115 | A1 | * | 2/2007 | Quigley et al. ................ 600/471 |
| 2007/0123935 | A1 | * | 5/2007 | Myers ............................ 606/222 |
| 2008/0294160 | A1 | * | 11/2008 | Garito et al. ................... 606/46 |

* cited by examiner

*Primary Examiner* — Kathleen Holwerda
*Assistant Examiner* — Sarah Simpson
(74) *Attorney, Agent, or Firm* — Kolisch Hartwell, PC

(57) ABSTRACT

The present invention relates to an apparatus, device and a method for harvesting blood vessels, and in particular, to such an apparatus, device and method in which the internal mammary artery (IMA) is harvested for coronary artery bypass graft (CABG) surgery using a minimally invasive approach or a conventional procedure.

14 Claims, 17 Drawing Sheets

DEVICE FOR HARVESTING A BLOOD VESSEL

This application is a national phase of, and claims priority from, PCT Application No. PCT/IL2008/000885, filed on Jun. 29, 2008, which claims priority from U.S. Provisional Application No. 60/958,297, filed on Jul. 5, 2007, all of which are hereby incorporated by reference as if fully set forth herein.

FIELD OF THE INVENTION

The present invention relates to an apparatus, device and a method for harvesting a blood vessel, and in particular, to such an apparatus, device and method employing an ultrasonic blade.

BACKGROUND OF THE INVENTION

Heart disease is known as the leading cause of death in the United States. The National Center for Health Statistics reported over 2.4 million deaths in the US in the year 2001, with heart disease being the leading cause with 700,142 cases. This accounts for 38.5% of all deaths in the United States in that year. According to the National Institutes of Health, heart disease is also the leading chronic preventable disease in the US today, outpacing all other preventable conditions. In statistical terms, the number of US cases affected by heart disease is 64,400,000, or 22.6% of the US population, with an associated cost of the disease for 2004 exceeding $368.4 billion.

Heart disease is defined as any disorder that affects the heart's ability to function properly, and is most commonly caused by narrowing or blockage of the coronary arteries, which supply blood to the heart itself. The treatment for coronary artery disease is mainly by angioplasty and surgical revascularization, known as coronary artery bypass graft (CABG). Due to the nature of the disease, CABG has become one of the most commonly performed procedures in the world. According to the American Heart Association's Heart Disease and Stroke statistics, 467,000 CABG surgeries comprising 346,000 men and 121,000 women were performed in the United States in 2003. This number increased to about 600,000 cases in 2005.

During a CABG surgery, vessels are connected to the heart to bypass the coronary artery blockages. Of those vessels, or conduits, the internal mammary artery (IMA) is the primary and the most preferred by surgeons for the bypass procedure. The IMA is harvested from the chest wall near the sternum and attached to the heart to supply blood to the area supplied by the blocked vessel experiencing hypo-perfusion.

The IMA (also known as the internal thoracic artery or ITA) is a major conduit for use in coronary artery bypass graft. The IMA is located on the interior surface of the chest on each side starting from the neck down, originating at the subclavian artery and ending at the superior epigastric artery. The IMA supplies blood to the chest wall including the ribs, sternum and breasts.

The mammary artery is an important conduit for bypass surgery as it is an artery rather than a vein; accordingly it has the lowest risk of thrombosis and occlusion among all other conduits. Consequently the state of the mammary artery has important prognostic value, and a well harvested and good flowing mammary artery determines the successful outcome of the surgery.

One of the reasons the IMA is a preferred conduit for CABG is due to its special properties and characteristics that differentiates it from other vessels. For example, in the inner layer of the IMA, the endothelium is thicker in this artery compared to other arteries; therefore, this vessel is rich in endothelial cells. Endothelial cells are responsible for the arterial features of a vessel, being active in production of multiple substances that actively mediate the arterial wall activity and maintenance of the vessels integrity. Due to these specific properties, the mammary artery has the best outcome as a graft in CABG. These outcomes are translated as the patency rate of 90% in 10 years when a mammary artery is used as a graft compared to 50% patency rate of a vein graft. Therefore, when planning a CABG, a mammary artery graft is always preferred and is almost always attached to the most important coronary artery, the left anterior descending artery (LAD).

The first stage of CABG is the preparation of the conduits for bypass. This stage includes harvesting the mammary artery (IMA) from the chest wall and harvesting veins from the leg. Surgeons primarily use the conventional method where the chest cavity is opened.

During conventional CABG the surgeon opens the chest by sawing the sternum at the midline. The pleura covering the artery and the lungs is then opened or retracted laterally exposing the IMA. This procedure provides the surgeon with a direct visual of the IMA, while half of the chest is pulled back and elevated with a retractor. Once the IMA is exposed, the surgeon uses electrocautery to divide the artery with its accompanying veins and some tissue as a pedicle or as a single vessel (skeletonized). The IMA side branches are usually divided following the application of a metal clip close to their origin on the artery and cauterization on the chest side. When the artery is divided superiorly up to its origin and inferiorly down to its bifurcation, it is cut at its lower end and at this time its tip is prepared and ready to be attached to the coronary artery that is being bypassed This traditional technique can be used to harvest each of the mammary arteries, left and/or right. The conventional harvesting procedure takes 15 to 40 minutes. Complications associated with the conventional technique include injury to the vessel itself or to the chest wall. Vessel injuries include bleeding during or following the harvest, direct injury to the artery or thermal injury with decreased flow, while the thermal injury to the chest wall causes sternal wound hypoperfusion with and infection. Any such complications might impede vessel flow and leave it unusable as a conduit for bypass. Furthermore, opening the chest cavity itself is detrimental to the patient, both increasing the risk of the operation and also increasing the recovery time required.

Although minimally invasive techniques are available for harvesting the artery, such as the endoscopic technique which is used as part of the totally endoscopic coronary artery bypass (TECAB) surgery, these techniques have many drawbacks. For example and without limitation, the procedure requires extensive training, it is very time consuming and it requires expensive and specialized equipment. In this method robotic arms are used to harvest the IMA through small incisions on the side of the chest wherein visualization is facilitated by video means. Harvesting using the robotic technique lasts for 60 to 70 minutes. When compared to the conventional technique and despite the cosmetic advantageous, the risk of injury using the robotic technique is higher. The increased risk is primarily due to the limited field of view and limited range of motion of the robotic arms provided by this method. Furthermore, there is also a higher risk of bleeding during the harvest that may require further medical intervention, such as chest opening to control the bleeding.

A well harvested artery obtained with minimal damage to the chest wall has significant effects on postoperative course. As being a major blood supplying artery to the chest wall, there is some compromise of the chest wall blood supply after harvesting the artery and diverting the flow to the heart instead of the chest wall. The combination of this relative hypo-perfusion with surgical intervention serves as a risk for surgical wound infection, a complication that results in high morbidity and mortality rates. This risk is significantly higher in patients with diabetes (40% of CABG patients), who already suffer a microcirculation damage associated with diabetes.

SUMMARY OF THE INVENTION

There is an unmet need for, and it would be highly useful to have, an apparatus, device and method for harvesting a blood vessel by using an ultrasonic blade which will be capable to work also in a minimally invasive 25 approach, for example for harvesting of the internal mammary artery in preparation for CABG procedure.

The present invention overcomes these drawbacks of the background by providing an apparatus, device and method suitable for dissecting a blood vessel using either minimally invasive or conventional techniques. By 30 "dissecting" it is meant cutting, coagulating or harvesting the blood vessel or tissue thereof.

In some embodiments, there is provided an apparatus, device and method for harvesting the internal mammary artery (IMA) in a minimally invasive endoscopic procedure or alternatively in an open chest procedure.

A preferred embodiment of the present invention relates primarily to a system for performing IMA harvesting from the chest wall as a conduit for coronary artery bypass graft surgery. Preferably, the apparatus, device and method may be applicable for both open chest and minimally invasive techniques. The preferred embodiment of the present invention provides a heart surgeon with a fast and reliable tool that preferably shortens the harvesting time, therefore reducing the risk of injury. For example, the harvesting time experienced during a conventional open chest surgical procedure takes from 15 to 40 minutes, while using the robot assisted minimally invasive harvesting techniques requires 60 to 70 minutes; however, the device according to a preferred embodiment of the present invention is expected to reduce the IMA harvesting time, without limitation to optionally up to about 15 minutes, more preferably up to about 10 minutes and most preferably up to about 5 minutes.

Preferably, the present invention provides an apparatus, device and method for harvesting the mammary artery (IMA) either through conventional procedure having a fully open chest, or using minimally invasive surgery techniques through a small incision, in a fast and reliable fashion.

According to a preferred embodiment of the present invention the harvester is introduced to the chest cavity and placed in the appropriate harvesting site thereafter beginning to progressing along the mammary artery. Most preferably, the device according to the present invention dissects and divides the IMA preferably using a camera providing a real time depiction of the harvesting procedure (although optionally through direct visual contact by the surgeon, for example during open chest surgery).

Preferably and optionally, harvesting the IMA is facilitated with the use of an ultrasonic scalpel. Most preferably, the ultrasonic scalpel according to the present invention provides increased precision, minimal charring, minimal lateral thermal tissue damage, improved hemostasis and consequently lower risk of bleeding.

Preferably, an ultrasonic scalpel achieves coagulation and tissue dissection at lower temperatures than standard diathermy. Preferably, the potential advantages of ultrasonic scalpel includes less lateral tissue damage, minimal smoke and no electrical energy passed to or through the patient. Optionally, other forms of scalpel may be used, for example including but not limited to an optical scalpel, comprising lasers which may be integrated with the device of the present invention. Preferably the lasers are low power lasers, in place of the ultrasonic scalpel.

Preferably, the ultrasonic scalpel functions to convert electrical energy into mechanical energy resulting in longitudinal oscillation of the blade at about 45 KHz to about 500 KHz. Preferably, the ultrasonic scalpel achieves coagulation and tissue dissection at lower temperatures than standard diathermy.

Without wishing to be limited in any way, the device according to the present invention provides improved patient safety as no electric current is passed through the patient. Accordingly, the risks associated with the direct use of electric current are avoided. Preferably, the device according to the present invention prevents thermal injury to the IMA during the harvesting process. Thermal injury may also lead to increased risk of spasm, flow compromisation and malperfusion of the target coronary vessels following bypass.

Preferably, the apparatus, device and method of the present invention provides a short harvesting time which further minimizes the chest wall injury and reduces the extent to which the blood supply is compromised, therein lowering the risk of wound infection particularly important in high risk patient groups that may also suffer from one or more other diseases, for example including but not limited to diabetes, peripheral vascular disease, obesity and the like.

Unless otherwise defined, all technical and scientific terms used herein have the same meaning as commonly understood by one of ordinary skill in the art to which this invention belongs. The materials, methods, and examples provided herein are illustrative only and not intended to be limiting. Implementation of the method and system of the present invention involves performing or completing certain selected tasks or steps manually, automatically, or a combination thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
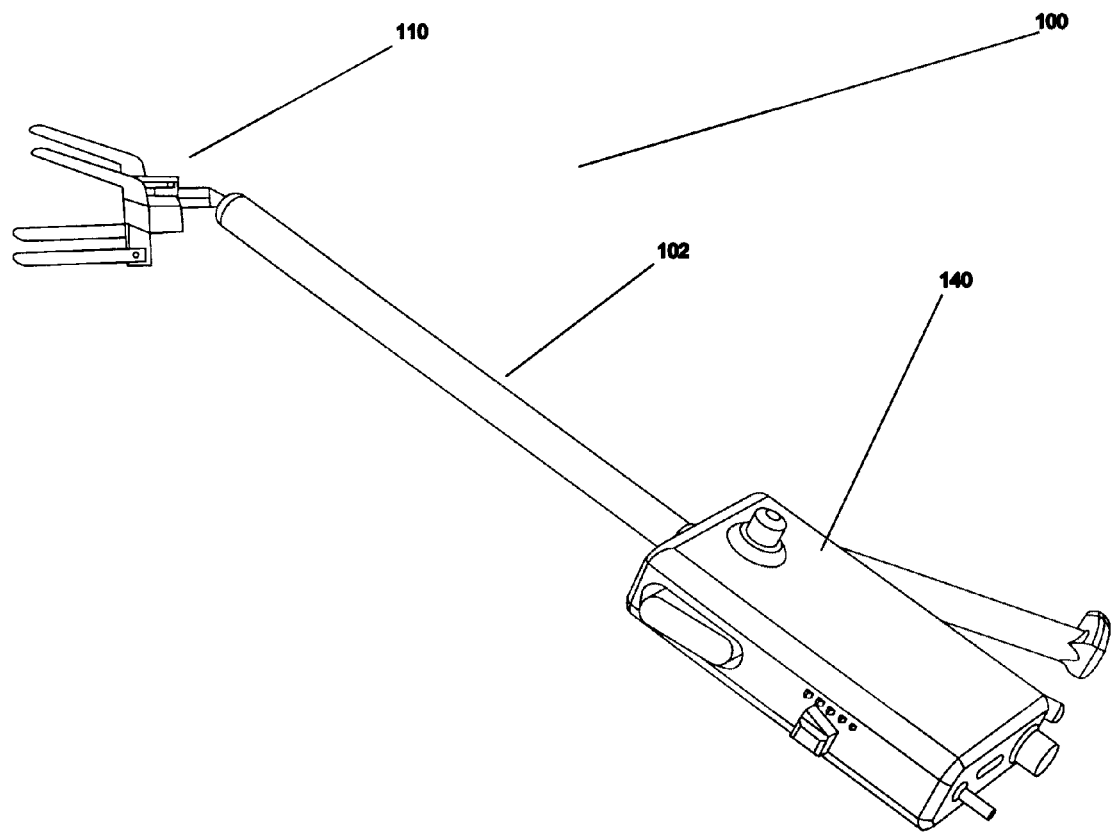
FIG. 1 is a perspective view of a schematic diagram of the IMA harvester according of an exemplary device according to the present invention.

The present invention is of an apparatus, device and method for dissecting a blood vessel, for example for efficient harvesting of the IMA artery in preparation for CABG. The principles and operation of the present 5 invention may be better understood with reference to the drawings and the accompanying description.

A preferred embodiment of the present invention provides for a device for efficient harvesting of the internal mammary artery (IMA) in preparation for CABG. Preferably, the device of the present invention 10 comprises a dissector head, a controllable arm and a control unit. Optionally, auxiliary devices may be coupled to the device of the present invention. Preferably, the auxiliary devices act as accessories to the device of the present invention. For example, auxiliary devices may optionally include but is not limited to a computer, display, processor, memory, 15 auxiliary power source, optical energy source, RF power source, communication port, ultrasound power source, ultrasound generator, ultrasound transducer (preferably a piezoelectric transducer) or the like.

Preferably, the dissector head is fluidly connected to the controllable arm that is then stably connected to the control unit. Preferably, the 20 connection between the dissector head and the controllable arm is mediated by at least one or more connectors preferably providing full range of motion of the dissector head relative to the controllable arm. Optionally, a plurality of connectors may be used to provide a full range of motion, preferably providing 180 degree range of motions between the controllable arm and 25 dissector head. For example, the connector mediating the fluid connection between the dissector head and the arm may optionally include but is not limited to any type of joint such as a ball and socket joint, a rotating hinge, a hinge, pneumatic actuators or the like as is known in the art.

Optionally, at least one or more connectors may be controlled 30 automatically, manually, or semi-automatically. For example, manual control may be facilitated by a user's control of the range of motion optionally utilizing a grip lock to set a given range of motion or lock on a particular position. Similarly, automatic and semi-automatic control may be facilitated by the use of at least one or more motors to control the relative position of the dissector to the arm, preferably in a full 360 degree range of motion.

The arm is preferably stably fixed to the control unit. Optionally, the range of motion of the connection between the arm and dissector is controlled by the control unit. Most preferably, the control unit comprises manual, semi-automatic and automatic means for controlling the range of motion of the dissector head relative to the arm.

Preferably, the dissector head according to the present invention is adapted for dissecting a blood vessel, for example for dissecting and harvesting the IMA from the chest wall. Optionally and preferably the dissector head comprises two parallel jaws connected on either side of the controllable arm, therein preferably forming a right and a left jaw, respectively. Preferably the right and left jaw are separated by up to about 5 cm. Most preferably the jaw separation distance is controllable ranging from about 2 mm to up to about 5 cm, although depending upon the location and size of the camera, the minimum jaw separation distance is preferably at least about 1 cm.

Furthermore, the size of the pedicle preferably ranges from about 5 mm to about 5 cm, more preferably from about 1 cm to about 4 cm.

Preferably, each jaw set comprises two extending arms protruding from a base that preferably perpendicular relative to the horizontal plane of the controllable arm. Optionally, each protruding arm is about 2 cm to 5 cm long, most preferably each protruding arm is between 2 cm to 4 cm long and most preferably it is about 3 cm long. Optionally the base is up to 5 cm in length, optionally it is between about 3 cm and 5 cm, preferably the base is at least 3 cm in length, and most preferably it is 4 cm long.

Preferably, the horizontal distance between the left and right jaws is controllable and mediated by a controllable connector. Preferably the right and left jaw are separated by up to about 5 cm. Optionally, the jaw separation distance is controllable ranging from about 2 mm to up to about 5 cm, although as noted above, depending upon the size and location of the camera, the minimum distance is preferably at least about 1 cm. Most preferably, the controllable jaw separation distance is between about 1.5 cm to up to about 3.5 cm from the internal side of the right and the left jaws. Preferably, the controllable connector provides at least one or more, and preferably all, of vertically oriented pivoting, vertical and horizontal positioning control of the right and left jaws. For example, the controllable connector may be a motorized connector having control means at the control unit for example including but not limited to a joystick, dial, peddle or button. Optionally, the controllable connector may form a bridge to horizontally connect the right and left jaws.

Preferably, each jaw set comprises two extending jaw arms protruding from a base that is preferably perpendicular relative to the horizontal plane of the controllable arm. Optionally a first jaw arm is fluidly connected to the vertical base, preferably forming an obtuse angle optionally about 90 degrees to about 120 degrees relative to the base. Optionally, the base and the first extension (jaw arm) form a single member, optionally referred to as the superior jaw. The superior jaw is optionally and preferably fixed. Optionally, a second jaw arm forms an inferior jaw that is preferably fluidly connected to the jaw base. Optionally, the second jaw arm is pivotally connected to the base with a pivot preferably providing the inferior jaw arm controllable motion relative to the jaw base. Optionally and preferably, the inferior jaw movement causes an object to be dissected with a dissecting modality, preferably an ultrasonic scalpel, such as for example including but not limited to the pedicle, or the like tissue, to be squeezed between the fixed superior jaw arm and the movable (preferably pivotable) inferior jaw arm. Preferably, the inferior jaw member movement is pivoted relative to the base provides the dissector head with the ability to control the jaw opening between the inferior and superior jaw members. Optionally, the jaw arm movement provides a scissor like motion.

Optionally both superior and inferior jaw arms may be individually pivotally joined at the common base. Optionally, the superior jaw may be pivoted at the upper portion of the base while the inferior jaw may be pivoted at the lower portion of the base. Also optionally, each jaw arm is attached to the base by an offset; if pivotal motion is provided, preferably pivoting occurs at the offset. Alternatively, pivoting may occur between the jaw arm and the offset.

Preferably the parallel jaws are used to manipulate and dissect the IMA from the surrounding tissue by forming scissor like movements along the length of the harvested artery, most preferably the IMA. Preferably, dissection and harvesting of the IMA is provided by an ultrasonic scalpel blade that preferably extends at least partially along the inferior edge of the superior jaw. Optionally, the ultrasonic scalpel blade edge extends alternatively on the superior edge of the inferior jaw or jaws.

Also optionally the superior edge of the inferior jaw features an ultrasonic blade; however preferably the superior edge of the inferior jaw features a fixed blade. The two positions may also optionally switched, in which the superior jaw features the fixed blade and the inferior jaw features the ultrasonic scalpel blade. Each such ultrasonic scalpel blade preferably features a transducer although optionally two such blades may share a transducer.

Optionally, the jaw arms (superior and inferior) are closed before the ultrasonic scalpel blade is activated; also optionally such activation may be manual or automatic.

Preferably and optionally, the interior face of at least one jaw arm comprising an ultrasonic blade providing an ultrasonic scalpel edge along the interior face edge of the jaw arm. Most preferably, the interior face of the jaw arm which features the ultrasonic scalpel comprises the ultrasonic transducer providing one or more ultrasonic scalpel edges.

Optionally, the jaws may be further provided with an extension of the ultrasonic blade extending to the distal end of at least one jaw arm. Preferably such an extension is provided for the superior jaw arm.

Preferably, the ultrasound transducer producing the ultrasonic energy in the scalpel edges may be fixed in the arm or control unit. Preferably, the ultrasonic scalpel utilized is as known and accepted in the art. Preferably, the ultrasound transducer produces a frequency of about 45 KHz to about 500 KHz.

Most preferably, an ultrasonic scalpel is provided on each of the right and left jaws and on each of the respective jaw arms. A preferred embodiment of the present invention comprises a dissection head with a plurality of ultrasonic scalpel surfaces; most preferably, four scalpel surfaces are featured on the interior face of each of the jaw arms.

Preferably, the distance between the right and left jaws is controllable and most preferably the distance may be defined based on the anatomy of the harvested IMA. Optionally, the distance between the right and left jaws is automatically adjusted but is preferably manually adjusted, optionally and preferably according to the IMA anatomy. This adjustment is preferably performed upon entry on the chest at the beginning of the harvest procedure and is more preferably only performed once. Optionally and preferably, the distance between the right and left jaws is manually adjusted, preferably by a surgeon, according to IMA anatomy. Most preferably the distance between the right and left jaws is controllably adjusted upon entry into the chest wall.

Preferably, the dissector head movement is controllable throughout the IMA harvest. Most preferably, the dissector head movement is controllable allowing it to progress along the length of the IMA and in keeping with the IMA anatomy, chest curvature, or the changes in angles. Optionally, the dissector head movement is automatically determined. Optionally, the dissector head movements are manually controlled.

Most preferably, the jaws are manually activated by an operator handle, preferably disposed in the control unit. Preferably the operator handle is operated by the surgeon and is a manual procedure. Most preferably, the manual manipulation of the operator handle are translated to the motion of the right and left jaw. Most preferably, such manual manipulation activates the jaws and the ultrasound transducers to generate an ultrasonic scalpel edge along the interior edge of each of the jaw arms while providing them with scissors like motion along the IMA path. Preferably, the operator handle provides the dissector head with sufficient degrees of freedom providing motion resembling that of a wrist.

Preferably, the dissector head comprises a bridge that connects the right and left jaws providing a means for fixing the jaws relative to one another and relative to the controllable arm. Optionally, the bridge may comprise a camera, light source, horizontal hinge, vertical hinge, pusher (described in greater detail below), and a controllable connector.

Optionally, the bridge may form a means for connecting the controllable arm to the dissection head as discussed above. Preferably, the bridge provides both vertical and horizontal motion providing a user with controllable range of motion.

A preferred embodiment of the present invention comprises a pusher that is preferably disposed between the right and left jaw of the dissector head. Most preferably, the pusher is disposed adjacent to the right jaw. The pusher provides a means to manipulate the IMA directly, while keeping the arterial tension during IMA harvesting. The pusher comprises a telescopic rod, an ultrasonic scalpel blade and a motor. Most preferably, the distal end of the pusher is provided with an ultrasonic scalpel to manipulate arterial branches of the IMA as the dissector advances along the length of the IMA.

As its name suggests, the pusher pushes the artery downward, thereby maintaining tension and also straightening the artery for ease of cutting and harvesting. In addition, the pusher may be used to push away redundant tissue. The redundant tissue might be confusing and may be misleading for the surgeon without maintaining the artery under tension in a straightened position. Also if a camera is present, the pusher may be used to maintain the line of sight of the camera.

Preferably the pusher motor is utilized to control both the telescopic and vertical movements of the telescopic rod.

Optionally and preferably, the movement and range of motion of the pusher are controllable by controlling the pusher motor. Preferably, the control means is provided by the control unit and may for example include but is not limited to joystick, dial, button, switch or the like means to control at least one or more preferably a plurality the pusher's range of motions. Optionally, the pusher motor is an electrical actuator motor, activated by switch or joystick on the control handle.

Optionally the telescopic rod is extensible up to about 3 to 4 cm forming an ultrasonic scalpel edge of about 12 mm.

A preferred embodiment of the dissector head according to the present invention comprises at least one camera optionally disposed on the dissection head bridge. Most preferably, the dissector head comprises a camera providing an operator with a visual depiction of the harvesting process as it is taking place. A camera preferably provides a visual depiction of the IMA anatomy allowing the operator to properly manipulate the dissector within the chest cavity, while monitoring the dissector's movements along the IMA path. Preferably, the camera utilized is a digital pin hole camera that may be disposed with the body and most preferably sufficiently small to allow use within the chest cavity. Optionally, the camera is a state of the art camera such as that utilized in endoscopic procedures or the same as used in the digital webcams or camcorders.

Most preferably, the camera comprises a light source providing the operator with sufficient field of view. The light source is preferably a state of the art light sources as is known and accepted in the art, for example including but not limited to a LED (light-emitting diode), fiber optic or the like. Optionally, the light source may be integrated with the camera. Optionally, the light source may be independent of the camera.

Most preferably, the camera's field of vision may be visualized on an auxiliary display screen. Optionally, the camera may be connected to the display screen by wired or wireless means as is known and accepted in the art. For example, the camera may be linked to an external display screen 5 using a USB (Universal Serial Bus) connection through an appropriate port disposed on the control unit.

An optional embodiment of the present invention provides for a plurality of cameras disposed within the dissector head. Optionally, at least one or more cameras may be disposed on the inferior or superior jaw arms; however, as at least the tips (or latter portions) of the jaw arms are to be inserted into the tissue, the camera placement should be such that the functionality of the arms and also of the camera(s) is not significantly reduced or altered. Optionally, at least one or more camera may be disposed along the pusher.

An optional embodiment of the present invention provides for at least one camera that may be interchangeably placed between various location within the dissector head, for example including but not limited to right jaw, left jaw, pusher, base, bridge, jaw arm, inferior jaw arm or the like.

A preferred embodiment of the present invention provides for a control unit that preferably provides control for the different facets and mechanisms of the dissector head. Most preferably, the control unit comprises a plurality of control switches and buttons to control the movement of the pusher motor and jaws, providing power to the ultrasonic scalpel, provides means to connect to the camera to an external display.

The control unit preferably comprises a power switch, joystick, manual operator handle, locking handle and a plurality of auxiliary ports.

Preferably, the joystick is utilized to control the activity of the pusher motor providing both telescopic and vertical movement to the pusher as well as controlling the ultrasonic scalpel preferably disposed therein.

Preferably, the manual operator handle provides an operator means to manually maneuver the jaws along the length of the IMA.

Preferably, the locking handle provides an operator means to set the position of the dissection head once it has been set.

Preferably a mains power switch provides power to the system particularly for the automatic manipulation of the jaws, ultrasonic scalpel.

Optionally and preferably the control unit comprises a plurality of auxiliary ports for example including but not limited to communication ports, power ports, USB (universal serial bus), wireless USB, wireless communication port, ultrasonic scalpel port, optical, IR (infrared), RF (radio frequency), fiberoptic, video, audio or the like peripheral port. Optionally, one or more ports provide the operator with the ability to couple additional tools to the device of the present invention.

Optionally, the device and apparatus according to the present invention is made in whole or in part from medical grade metals and/or plastics for example including but not limited to aluminum, titanium, stainless steel, nitinol or the like materials, composites or alloys thereof as is known and accepted in the art. The jaws are also preferably made of the above materials; the blades of the ultrasonic scalpel are preferably made of a metal, composite, alloy or other combination of metals; however, they may optionally be covered in plastic. Preferably, the materials used are sterile, and are optionally sterilizable (for example through autoclaving or another procedure) as is known and accepted in the art. Optionally, the embodiments of the present invention may be composed in whole or in part of single use or multi use materials.

Referring now to the drawings, please note that the same figure labels are used throughout the specification to refer to the same or similarly functioning components.

FIG. 1A shows an IMA harvesting device 100 according to the present invention comprising dissection head 110, arm 102 and control unit 140. Although harvesting device 100 is described as a device for harvesting 30 IMA, it should be noted that in fact it may optionally be used for many different types of tissue dissection and operations. Preferably, dissection head 110 is used within the chest cavity to harvest an IMA (not shown) wherein arm 102 is used to help navigate and direct dissection head 110 through the chest cavity while transferring control instructions, for example including but not limited to movement and positioning instruction and power source from control unit 140.

Figure 1B:
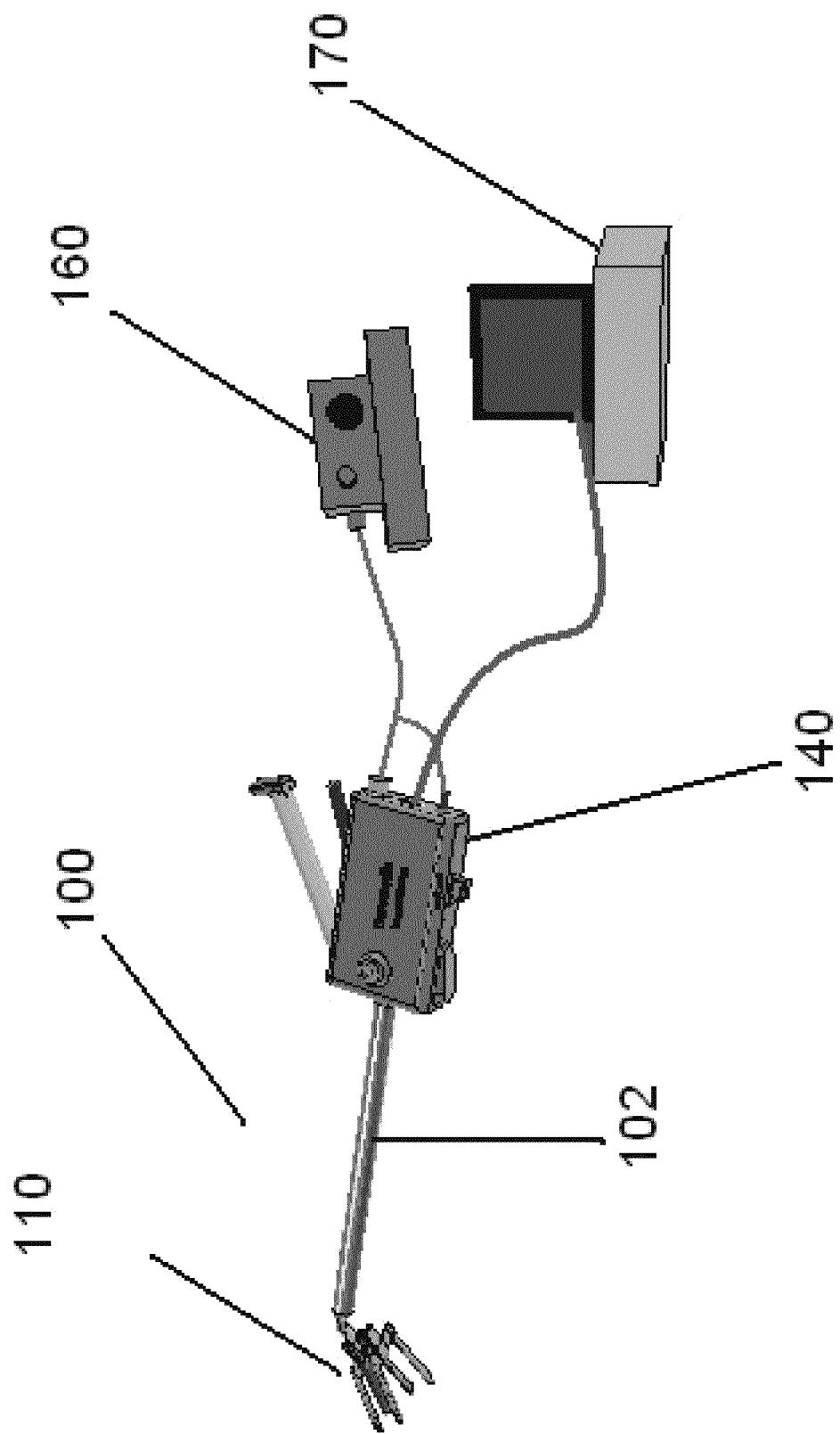

FIG. 1B depicts an apparatus 101 comprising IMA harvesting device 100 of FIG. 1A further comprising auxiliary devices through a plurality of auxiliary ports. For example, display 170 is preferably used to display the video captured through an optional camera (not shown) preferably mounted within dissection head 110. Ultrasound power source 160 is optionally and preferably attached through a different auxiliary port.

Figure 2:
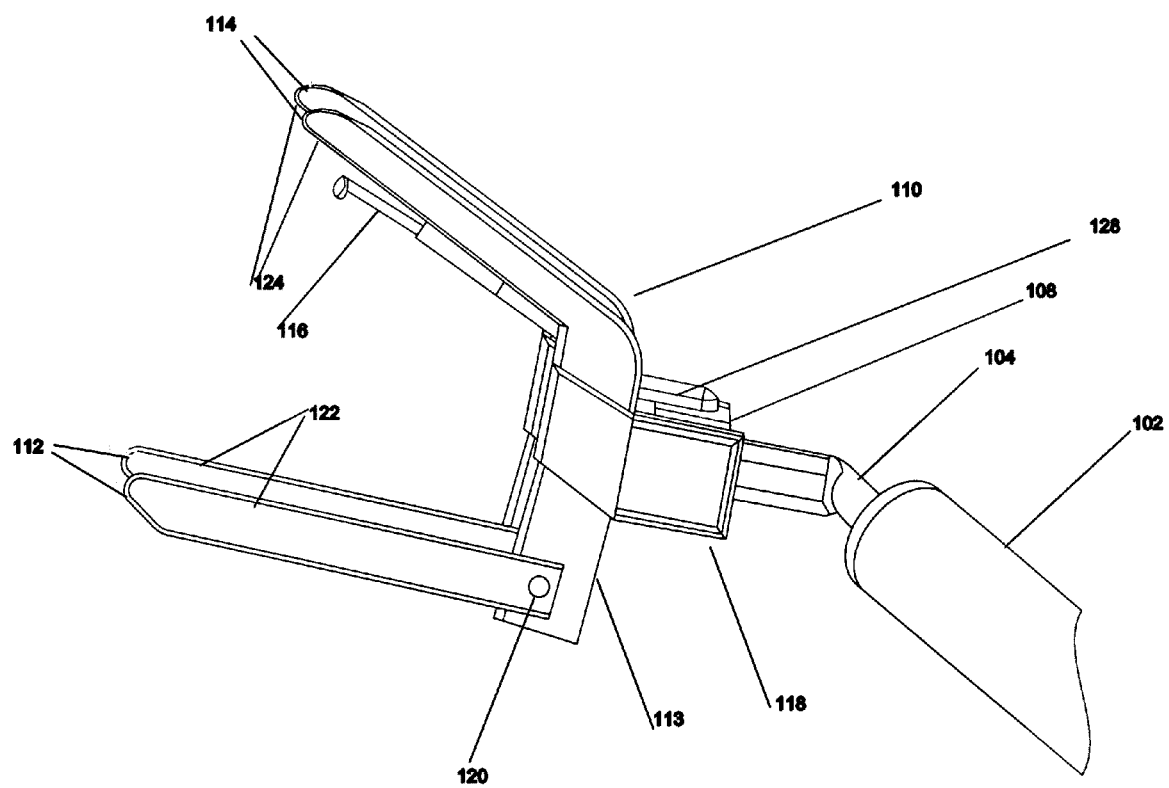
FIG. 2 is a side view of a schematic diagram of the arm of the IMA harvester according of an exemplary device according to the present invention.

FIG. 2 depicts a close up side view of dissection head 110 in greater detail. Dissection head 110 is controllably coupled to arm 102 through a moveable joint 104. Joint 104 may optionally be realized in the from of a ball and socket, moveable hinge, motor or the like that are optionally automatically controlled with a motor or more preferably manually controlled by an operator using control unit 140 (not shown).

Dissection head 110 comprises a pair of superior jaws 114 and inferior jaws 112 that are joined through a jaw base 113. Optionally, superior jaw 114 is fixedly joined with jaw base 113 while inferior jaw 112 is connected to jaw base 113 with pivot 120. Pivot 120 preferably provides inferior jaw 120 with rotation about the pivot axis allowing a user to control the opening formed between the superior jaw 114 and the inferior jaw 112. Pivot 120 therefore provides the movement of the inferior jaw 112 relative to base 113 and superior jaw 114 producing the scissor motion utilized for harvesting and dissecting the IMA (not shown).

One or both of superior jaw 114 and inferior jaw 112 optionally comprises an ultrasonic scalpel; in the embodiment shown, both superior jaw 114 and inferior jaw 112 feature such a scalpel for the purpose of illustration only and without any intention of being limiting. The inferior jaw 112 comprises ultrasonic scalpel 122 along its interior face edge. Similarly, superior jaw 114 comprises ultrasonic scalpel 124 along its interior face edge. Preferably, a plurality of ultrasonic face edges are utilized to dissect the tissue in harvesting the IMA; however, alternatively each of inferior jaw 112 and superior jaw 114 features only one ultrasonic blade edge (not shown). Also optionally, only inferior jaw 112 or superior jaw 114 is present, but features a plurality of ultrasonic blade edges (not shown). Also optionally, each such ultrasonic blade is exposed or is only partially covered by a "housing" (not shown), for example for greater ease of attaching and detaching the blades.

Optionally and preferably, at least one jaw of inferior jaw 112 or superior jaw 114 has at least two degrees of freedom with respect to jaw base 113 and/or arm 102. More preferably, one jaw (most preferably the jaw featuring an ultrasonic scalpel 122 or 124) has at least two degrees of freedom. Most preferably, the jaw only has two degrees of freedom.

Also optionally and preferably, each pair of jaws 112 and 114 has at least two degrees of freedom with respect to the arm 102.

Dissection head 110 further comprises pusher 116, preferably providing the dissected IMA with tension, thereby allowing the jaws 112 and 114 to continuously harvest without undue burden. Preferably, pusher 116 is telescopic and is moveable in the vertical axis. Preferably, the movements, both telescopic and vertical, provided by pusher 116 are mediated by pusher motor 128. Preferably, pusher motor 128 is controlled by control unit 140 (not shown). Optionally, the pusher motor 128 is an electrical actuator motor, activated by switch or joystick on the control handle (not shown).

Preferably, pusher motor 128 is disposed on bridge jaw 108 that joins jaw base 113. Jaw base 113 is further provided with a horizontal adjustment 118 preferably allowing jaw base 113 to move horizontally about bridge 108.

Figure 3:
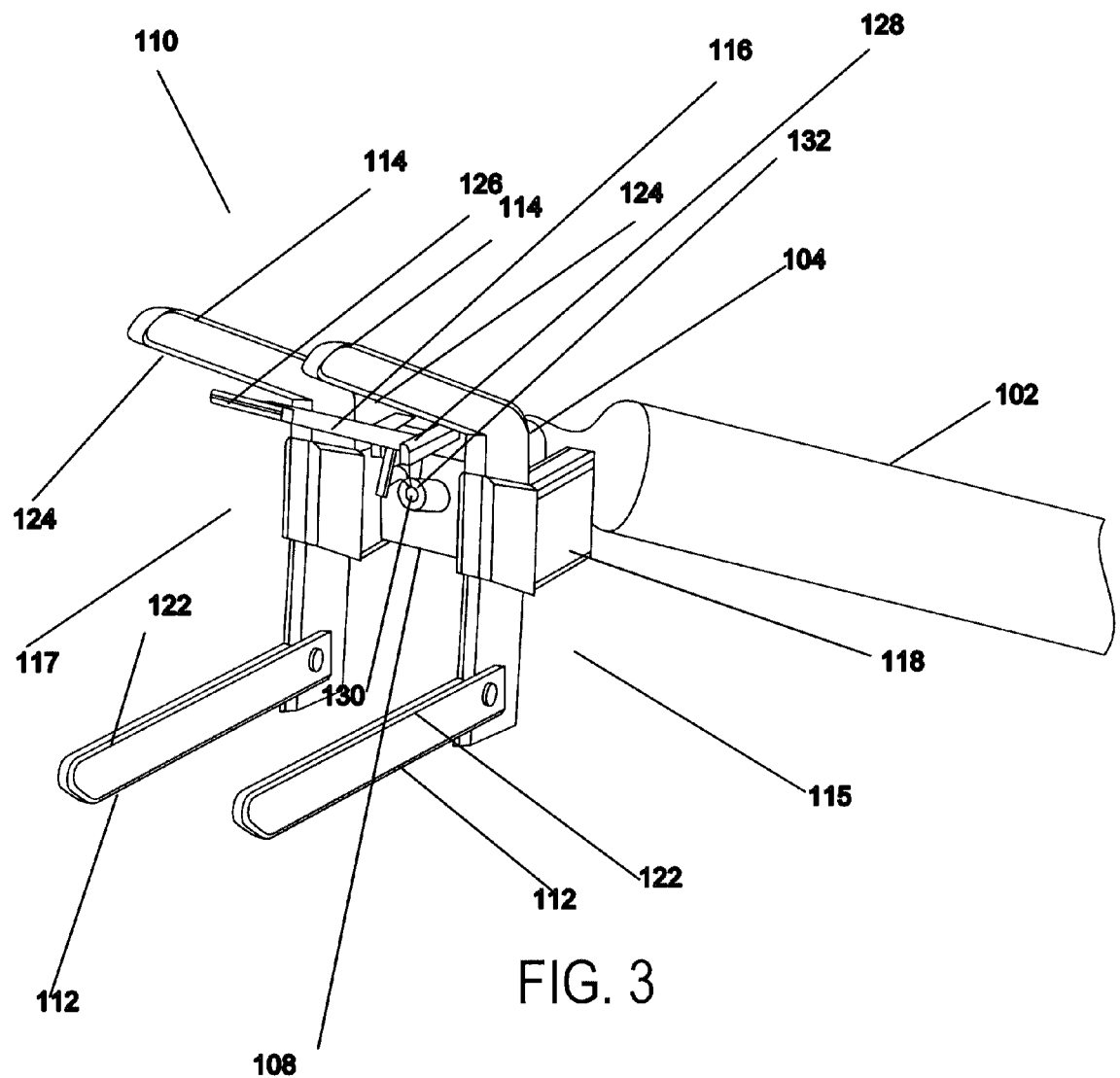
FIG. 3 is a close up perspective view of a schematic diagram of the 30 arm of the IMA harvester according of an exemplary device according to the present invention.

FIG. 3 depicts a close up perspective view of dissector head 110 according to a preferred embodiment of the present invention. The 30 perspective view reveals camera 130 and light source 132 that are optionally disposed on bridge 108 and between the right pair of jaws 115 and the left pair of jaws 117. Preferably, camera 130 is a pin hole digital camera comprising a light source 132. Camera 130 provides an operator with visualization of the harvesting procedure preferably in near real time, optionally and preferably content depicted by camera 130 may preferably be broadcast to an external display 170, as depicted in FIG. 1B. Optionally, no camera 130 is present and/or is detachably removable.

FIG. 3 further provides a closer depiction of pusher 116 that comprises an ultrasonic scalpel 126. Preferably ultrasonic scalpel is utilized to harvest an IMA (not shown).

Bridge 108 preferably mediates and connects left pair of jaws 117 and right pair of jaws 115. Bridge 108 further comprises horizontal adjustment 119 providing horizontal adjustment to control the distance between left pair of jaws 117 and right pair of jaws 115.

Figure 4:
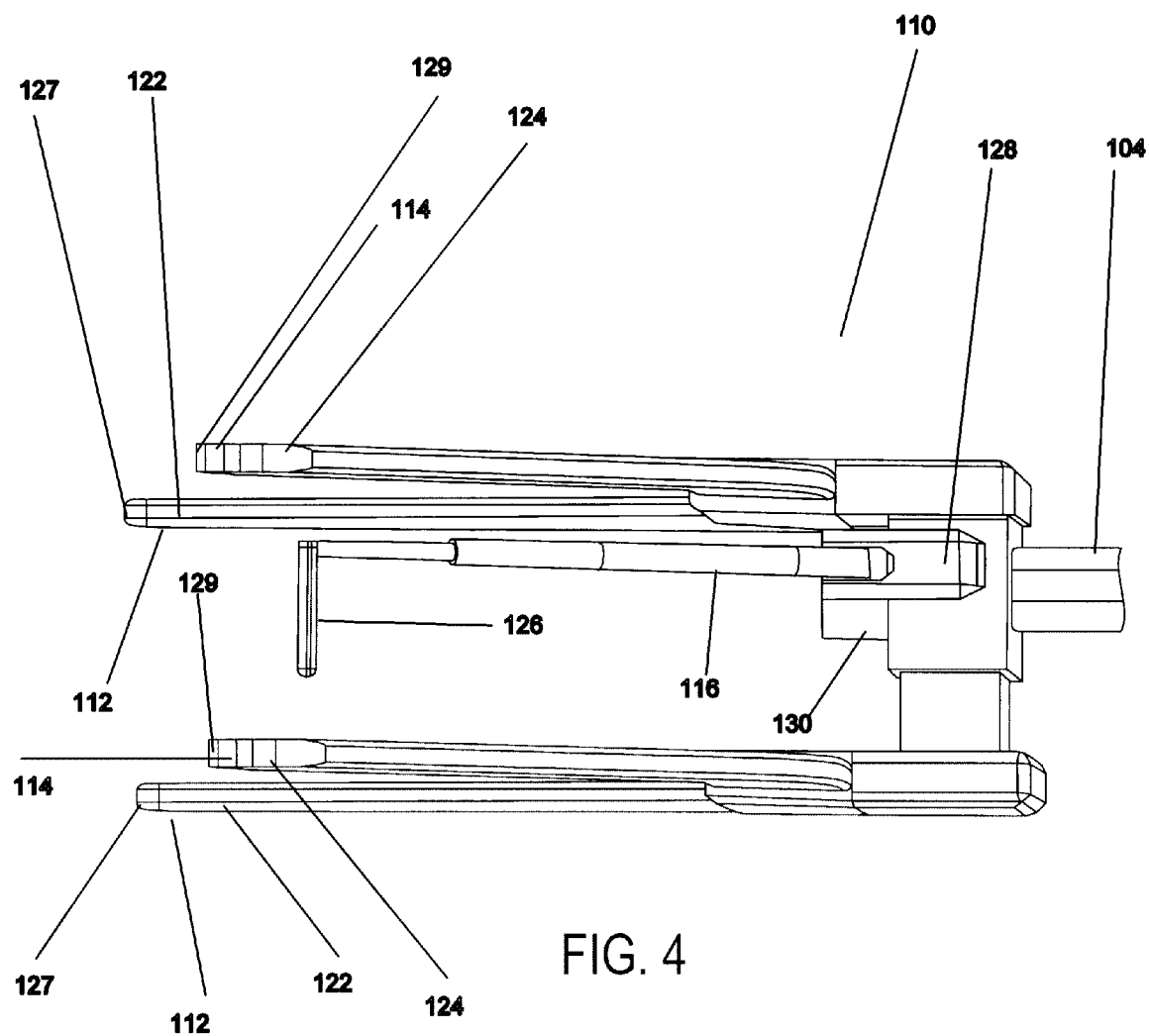
FIG. 4 is a top down view of a schematic diagram of the arm of the IMA harvester according of an exemplary device according to the present invention.

FIG. 4 is a top down view of the IMA harvester according to an exemplary embodiment according to the present invention wherein pusher 116 is more clearly depicted. Pusher ultrasonic scalpel 126 is preferably utilized to facilitate the harvesting of an IMA without damaging the harvested artery. Optionally, a further ultrasonic scalpel 127 and 129 may be disposed in an optional embodiment of the present invention at the distal edge of the inferior jaws 112 and superior jaws 114, providing a further means to dissect the artery.

Optionally and preferably, one or more (and more preferably all) of the components of dissector head 110 (according to any embodiment herein) are replaceable and/or disposable, most preferably including without limitation camera 130, the ultrasonic transducers (not shown), the pusher 116, inferior jaws 112 and superior jaws 114, and the blades of ultrasonic scalpels 126, 127 and 129.

Figure 5:
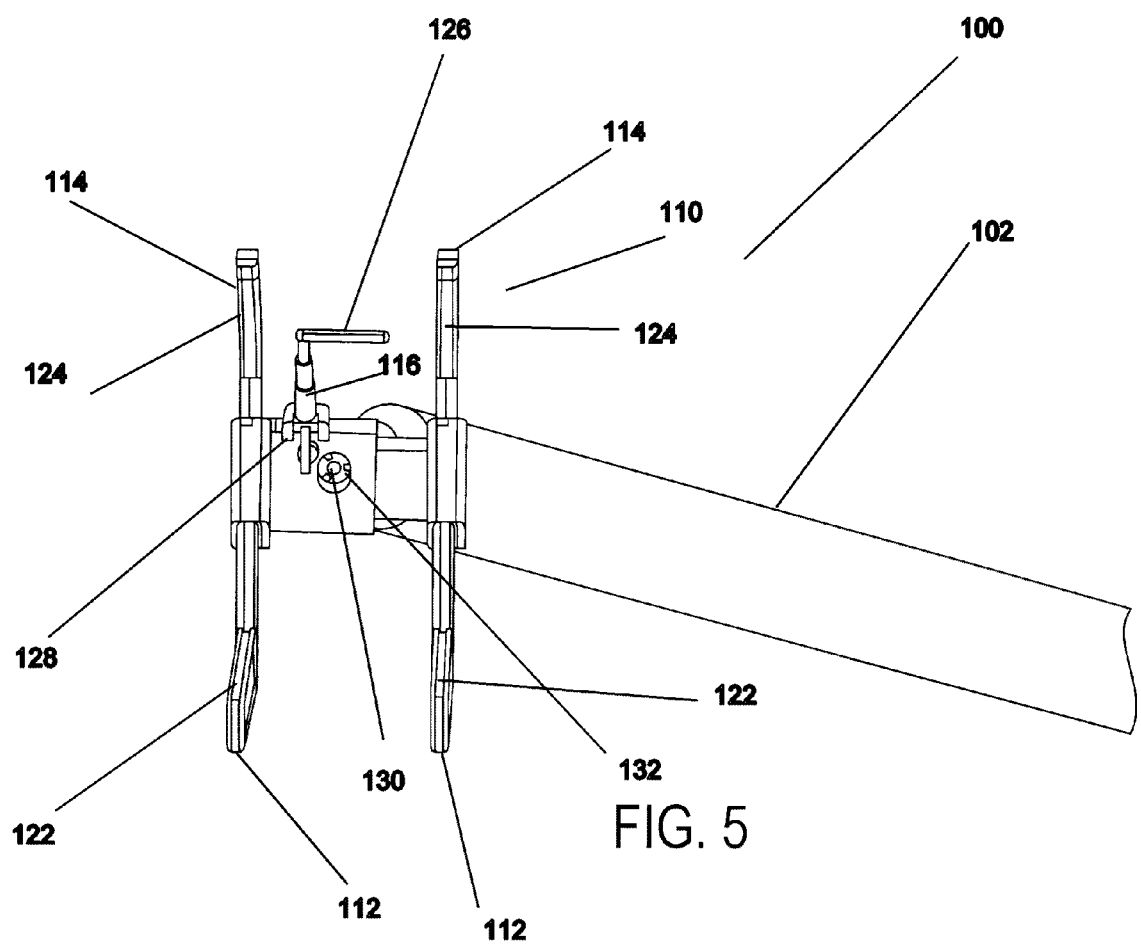
FIG. 5 is a close up frontal view of a schematic diagram of the arm of the IMA harvester according of an exemplary device according to the present invention.

FIG. 5 provides a close up frontal view of the harvester 100 according to an exemplary embodiment of the present invention.

Figure 6:
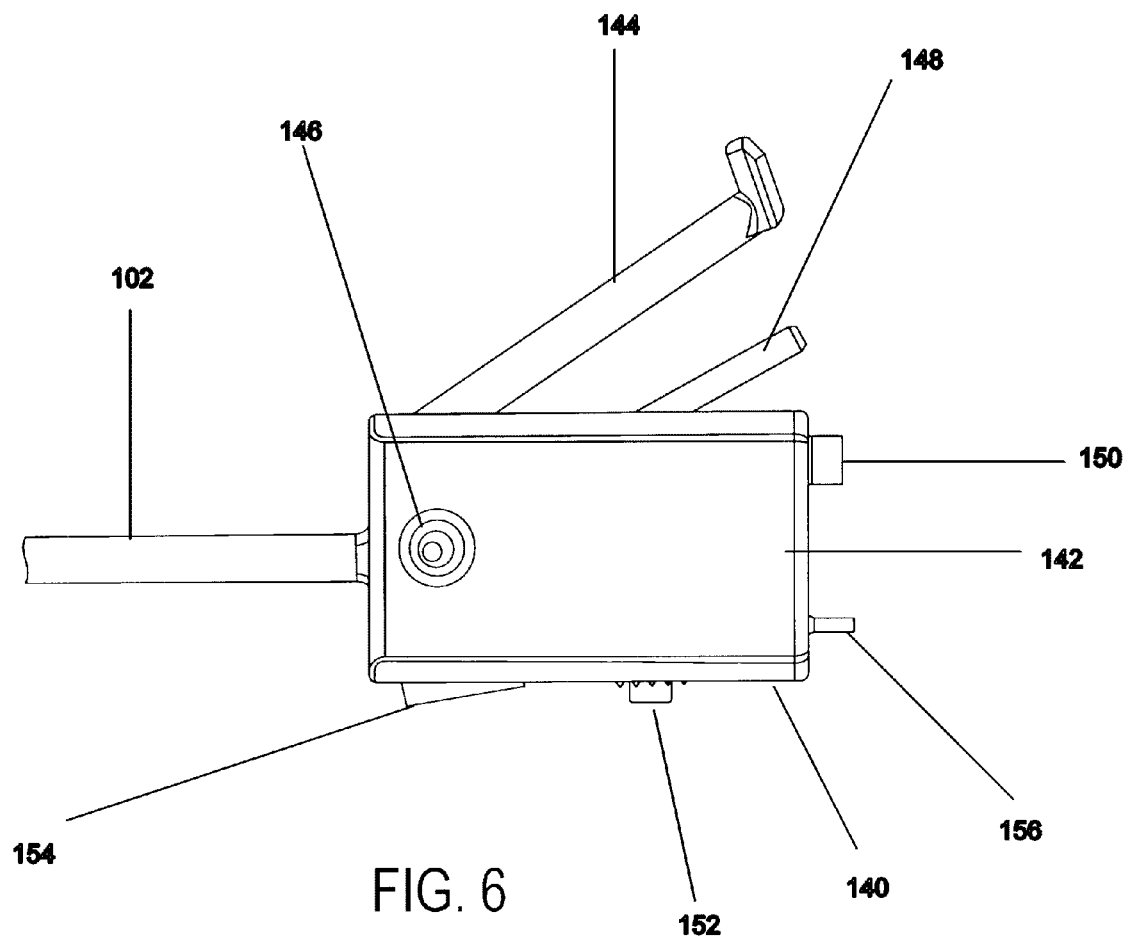
FIG. 6 is a close up planar view of a schematic diagram of the control box of the IMA harvester according of an exemplary device according to the present invention.
Figure 7:
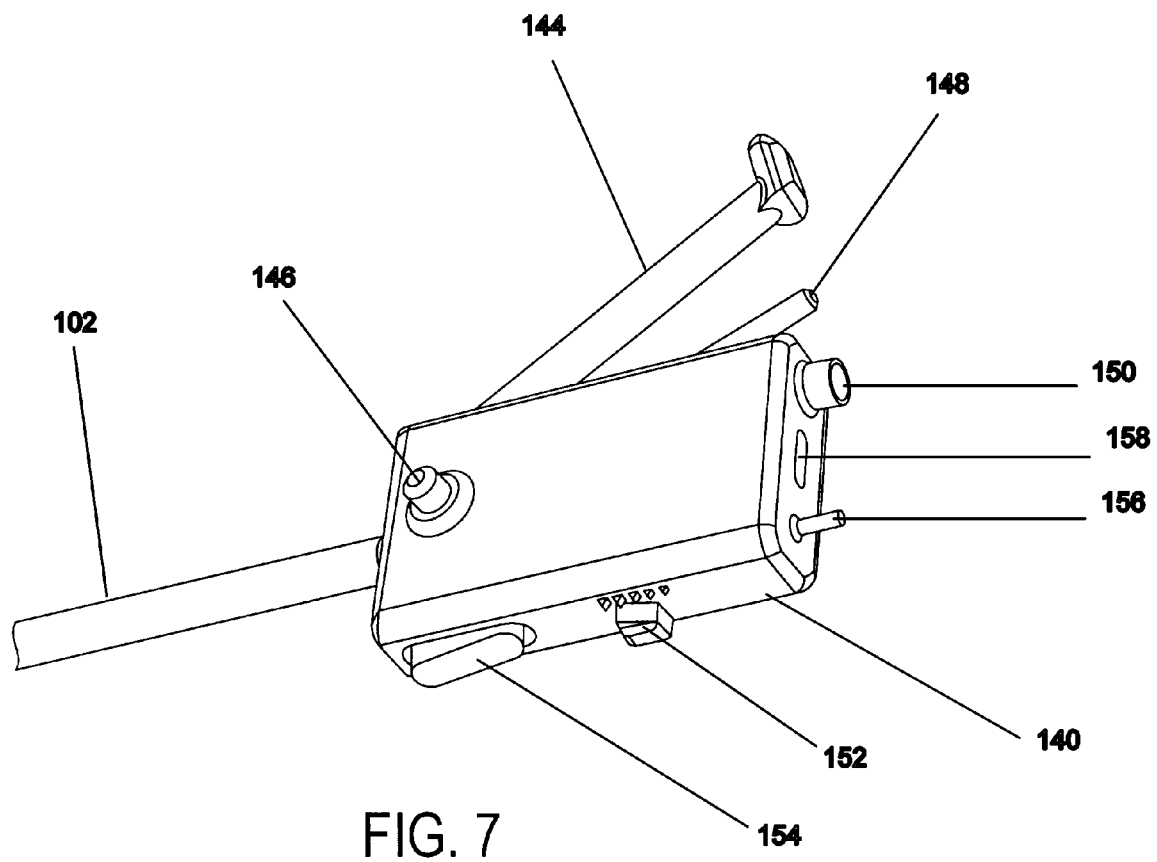
FIG. 7 is a close up perspective view of a schematic diagram of the control box of the IMA harvester according of an exemplary device according to the present invention.

FIGS. 6 and 7 provide close up planar view of control unit 140 of the harvester 100 according to an optional embodiment of the present invention.

A preferred embodiment of the present invention provides for a control unit 140 that preferably provides control for the different facets and mechanisms of the dissector head 110. Most preferably, the control unit 140 comprises a plurality of control switches and buttons to control the movement of the pusher motor and jaws, providing power to the ultrasonic scalpel, and optionally providing means to connect to the camera to an external display (if such a camera is present).

Control unit 140 comprises a controller 142, a power switch 154, pusher joystick 146 for controlling the movements of the pusher (not shown), manual operator handle 144, locking handle 148 (for locking the dissector unit or head (not shown)) and a plurality of auxiliary ports.

Preferably, pusher joystick 146 is utilized to control the activity of the pusher motor 128 (not shown) providing both telescopic and vertical movement to the pusher 116 as well as controlling the ultrasonic scalpel 126 (not shown) preferably disposed therein.

Preferably, the manual operator handle 144 provides an operator means to manually maneuver the jaws along the length of the IMA.

Preferably, the locking handle 148 provides an operator means to set the position of the dissection head once it has been determined.

Preferably a mains power switch 154 provides power to the system particularly for the automatic manipulation of the jaws, ultrasonic scalpel.

A plurality of auxiliary ports is optionally available through controller 142 as depicted in FIG. 1B. The present close up view depicts optional auxiliary ports for example including but not limited to mains power supply 156, a USB camera port 158 and the ultrasonic scalpel port 154.

Figure 8:
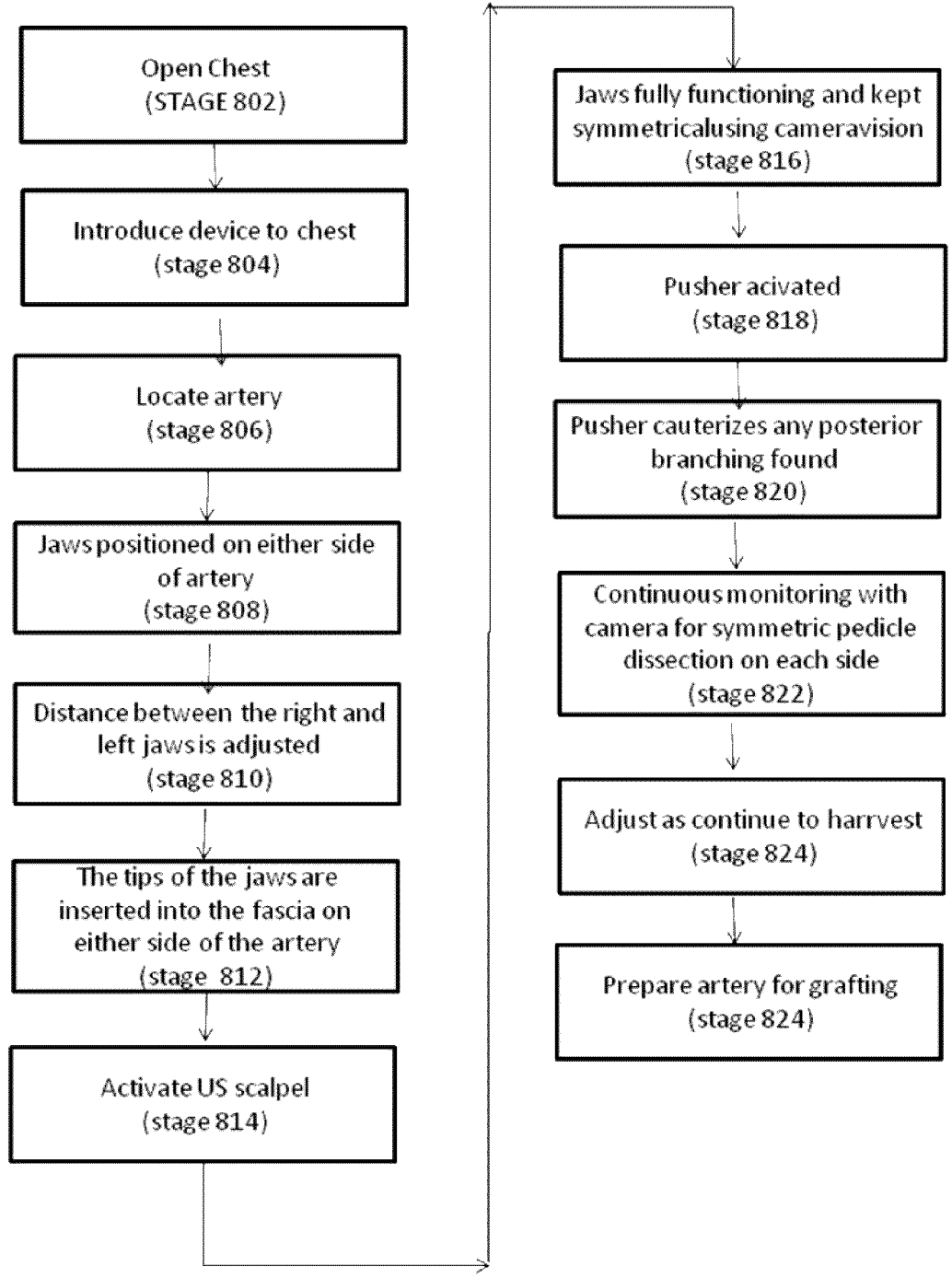
FIG. 8 is an exemplary method for harvesting an artery according to the present invention.

FIG. 8 depicts an exemplary method according to the present invention wherein the IMA is harvested in preparation for a CABG procedure. In stage 802 the chest is opened sufficiently to permit entry of the harvester device according to the present invention; optionally the chest may be opened through either thoracotomy or sternotomy or other means known and accepted in the art, or alternatively a small incision may be made for minimally invasive surgery. In stage 804 the harvester according to the present invention is introduced into the chest cavity. In stage 806 the artery is located optionally and preferably utilizing the camera disposed within the dissector head according to an optional embodiment of the present invention. However, if a minimally invasive technique is not being used, then the camera may optionally be omitted. In stage 808 the two jaws are positioned on each side of the artery, preferably at a location along the artery where the artery is most visible. Optionally and preferably during stage 808 the locking handle is placed and locked into place, most preferably until the artery's anatomy depicts need for realignment or handle locking, for example during stage 812 below for fine tuning. In stage 810 the distance between the right and left jaws are adjusted, preferably in accordance with the anatomy of the IMA being harvested. In stage 812 the tips of the jaws then inserted into the fascia on each side, possibly activating the ultrasonic scalpel to facilitate the entry and the jaws are activated slowly until slight development of the pedicle.

In stage 814 the jaws are incorporated with the ultrasonic scalpel edges on each side of the artery, and the camera (if present) is focused and pointed on the midline on the inferior surface of the artery.

In stage 816, full activation of the jaws is instituted, while the jaws are kept symmetrically on each side of the artery using the camera view and/or through visual control from the surgeon, for example for open chest surgery. In stage 818 the fascia is continuously divided and the flap develops further, the pusher is activated by the joystick in the control unit to keep the pedicle in tension downward making the jaws activities more efficient and separating the artery from the chest wall. In stage 820 the harvesting procedure continues with the aid of the pusher, jaws and optionally camera, while the operator looks for instances where IMA might have branches coming off on the IMA's posterior surface and penetrates to the chest wall, then this branch will be cauterized using an ultrasonic scalpel at the edge of the pusher which is controlled by the joystick in the handle.

The dissector is advanced proximally to the either side of the mammary artery while the motion of the jaws is continuing to complete the harvest. The active parts of the jaws with ultrasonic scalpel are located on the internal side of the jaws. Approximation and scissor movement of the jaws cuts and divides the mammary artery with its fascia on each side, while the branches on each side are cauterized with the ultrasonic scalpel.

In stage 822 the exact direction and location of the dissector is monitored either through direct visual contact by the surgeon, or optionally with the camera which is placed in between the jaws (for example for minimally invasive surgery). If the present, the camera is focused on the artery in the center of the field maintains the two jaws in parallel to the path of the mammary artery, and also maintains symmetrical pedicle dissection on each side.

In stage 824 as the harvest continues the device according to the present invention is adjusted to anatomy specific to the harvested IMA. For example, as the dissector proceeds, the curvature of the chest or the angles change and the dissector head will be adjusted accordingly during the progress.

In stage 826 the artery is disconnected from its distal end and preferably prepared for grafting by being divided at the distal end. The artery stays connected at its proximal end, while the distal end of the artery is then preferably attached to the heart.

Figure 9:
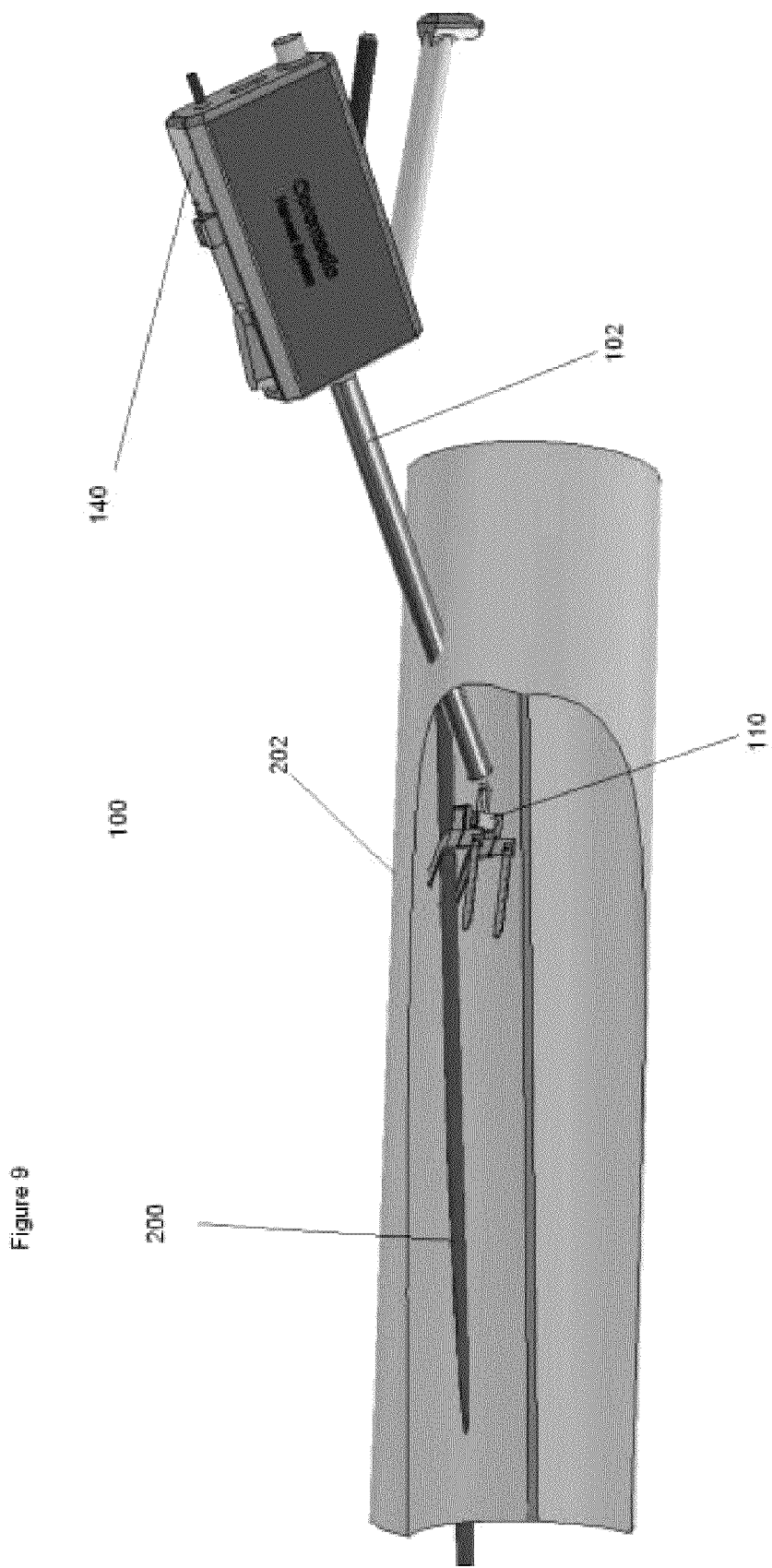
FIG. 9 is a perspective view of the device according to a preferred embodiment of the present invention while harvesting the IMA within the chest cavity.

FIGS. 9 to 13 provide a visual depiction of the use of device according to the present invention as described in FIG. 8. FIG. 9 is a depiction of the insertion of the IMA dissector 100 through the chest wall and placed adjacent to the IMA about to be dissected, effectively as described in Stages 802 to 808. IMA 200 is shown within the chest cavity 202 as dissector unit 110 (or head) is moved into position for dissection.

Figure 10:
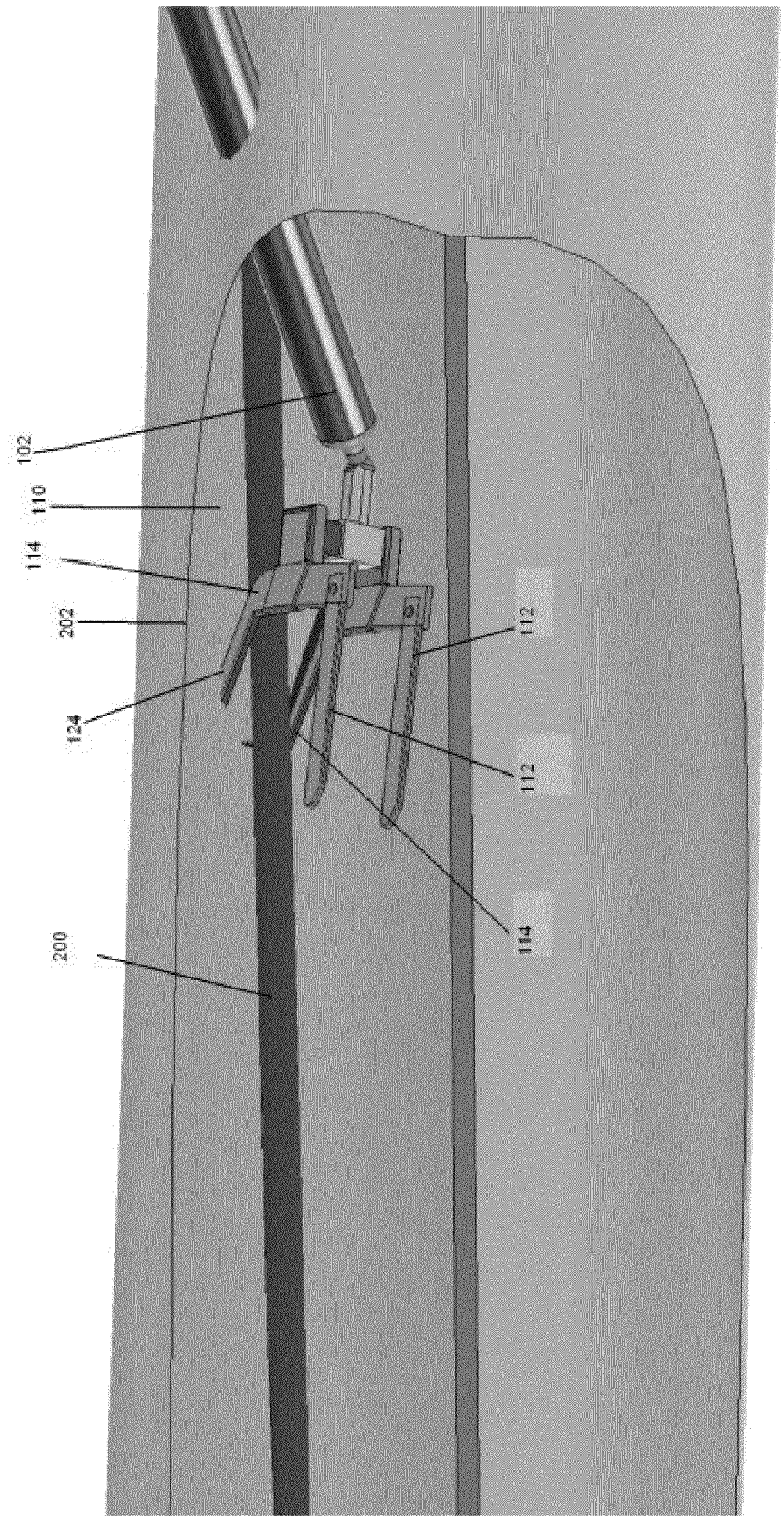
FIG. 10 is a close up view of FIG. 9 depicting the dissector of the present invention while harvesting the IMA.

FIG. 10 provides a close up view of FIG. 9 wherein dissector head 110 is activated to harvest IMA 200 within the chest cavity 202 using ultrasonic scalpel 124 on superior jaws 114 that surround IMA 200.

Figure 11:
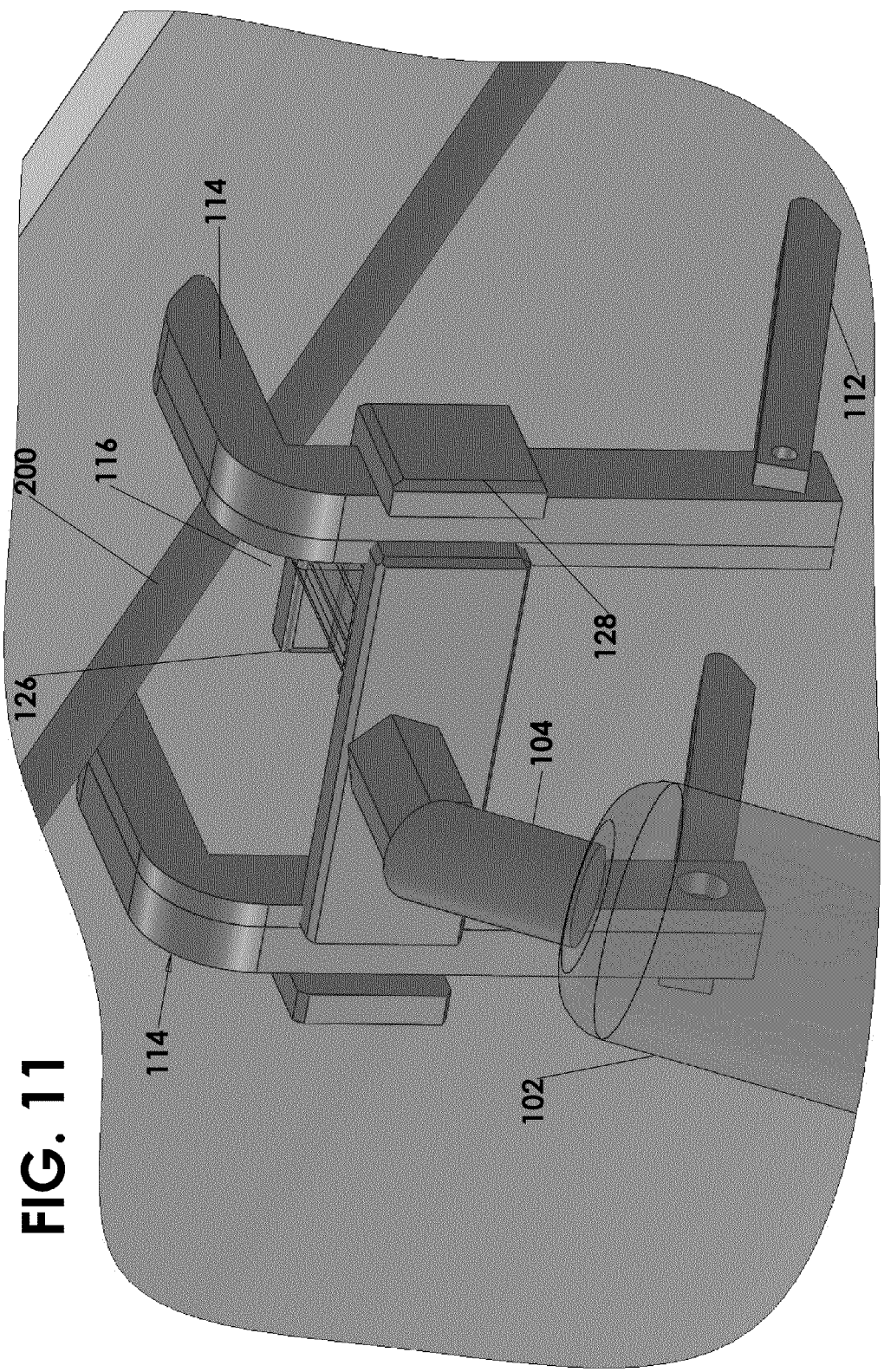
FIG. 11 is a back view of FIG. 10.

FIG. 11 provides a back view of FIG. 10 wherein IMA 200 is clearly visualized and is being harvested with the use of pusher 116 and pusher ultrasonic scalpel 126, while maintaining jaws 114 and 112 aligned around IMA 200, as depicted in Stages 816 to 822.

Figure 12:
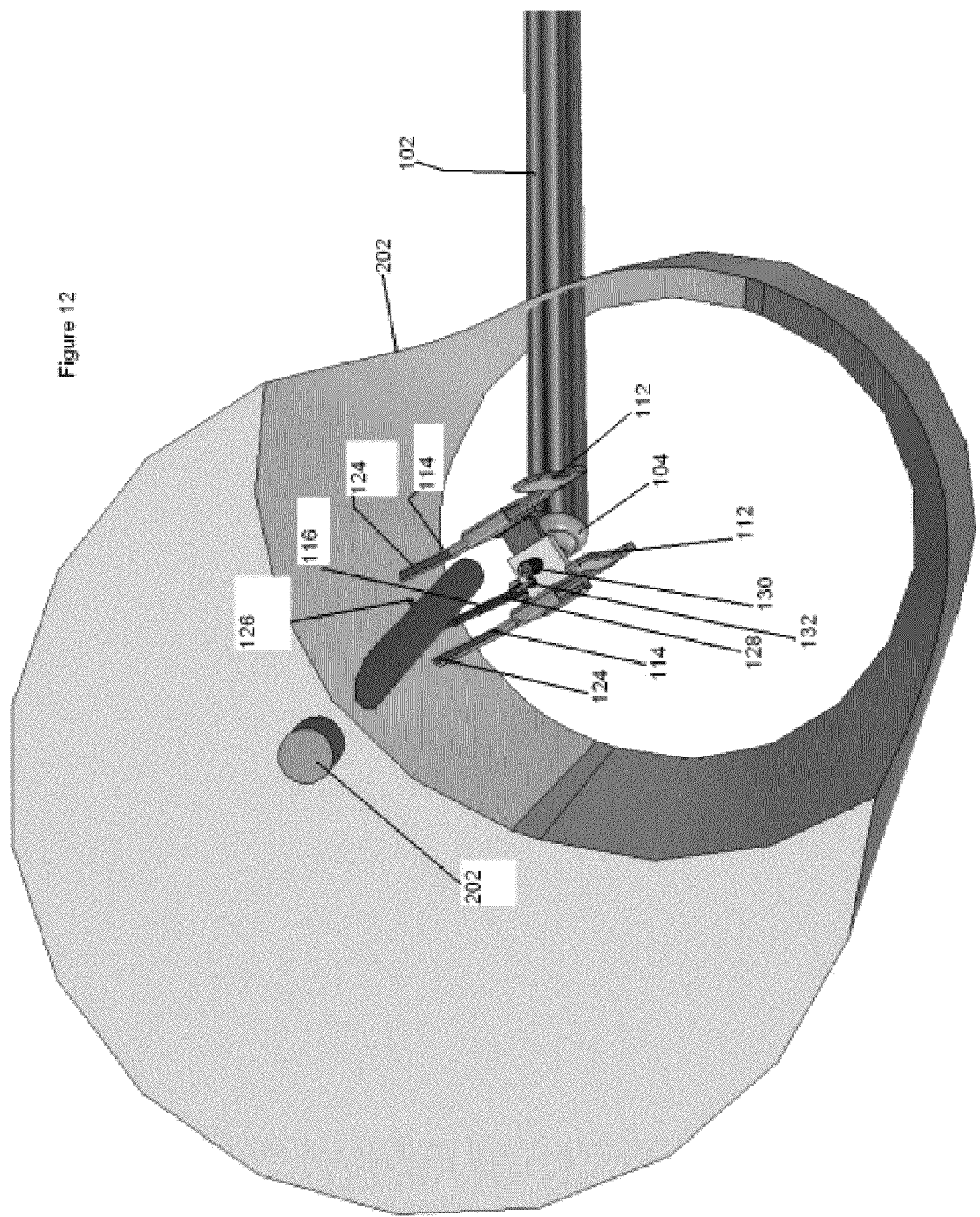
FIG. 12 is a frontal view of FIG. 10.

FIG. 12 provides a frontal view of FIG. 10 wherein camera 130 and pusher 116 are readily visualized in monitoring IMA 200 as depicted in Stage 822 of FIG. 8.

Figure 13:
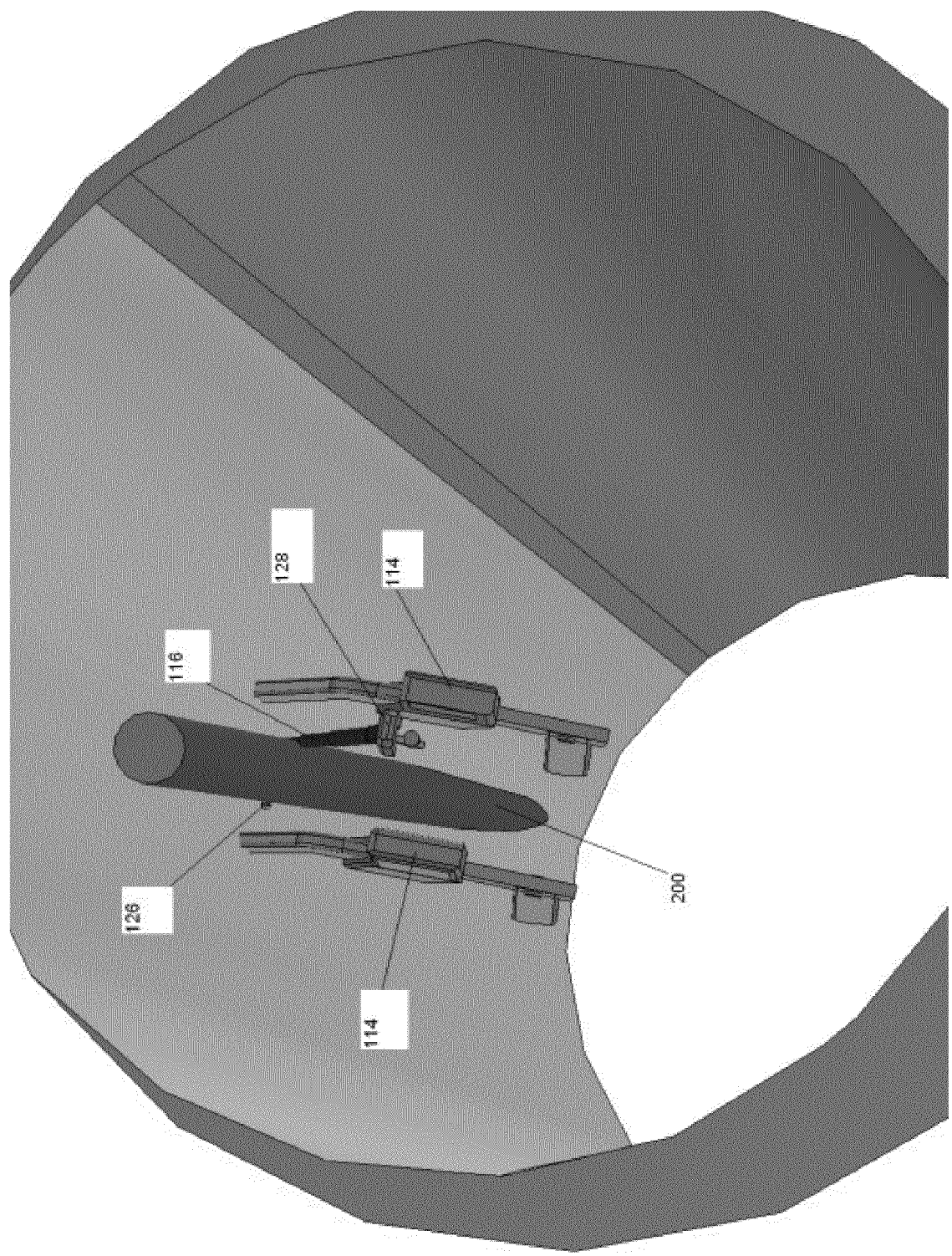
FIG. 13 is a perspective view of FIG. 10 taken from the harvester's camera according to an optional embodiment of the present invention.

FIG. 13 provides a physician view as depicted by camera 113, optionally and preferably visualizing IMA 200 on an auxiliary external monitor 170 of FIG. 1B (not shown).

Figure 14:
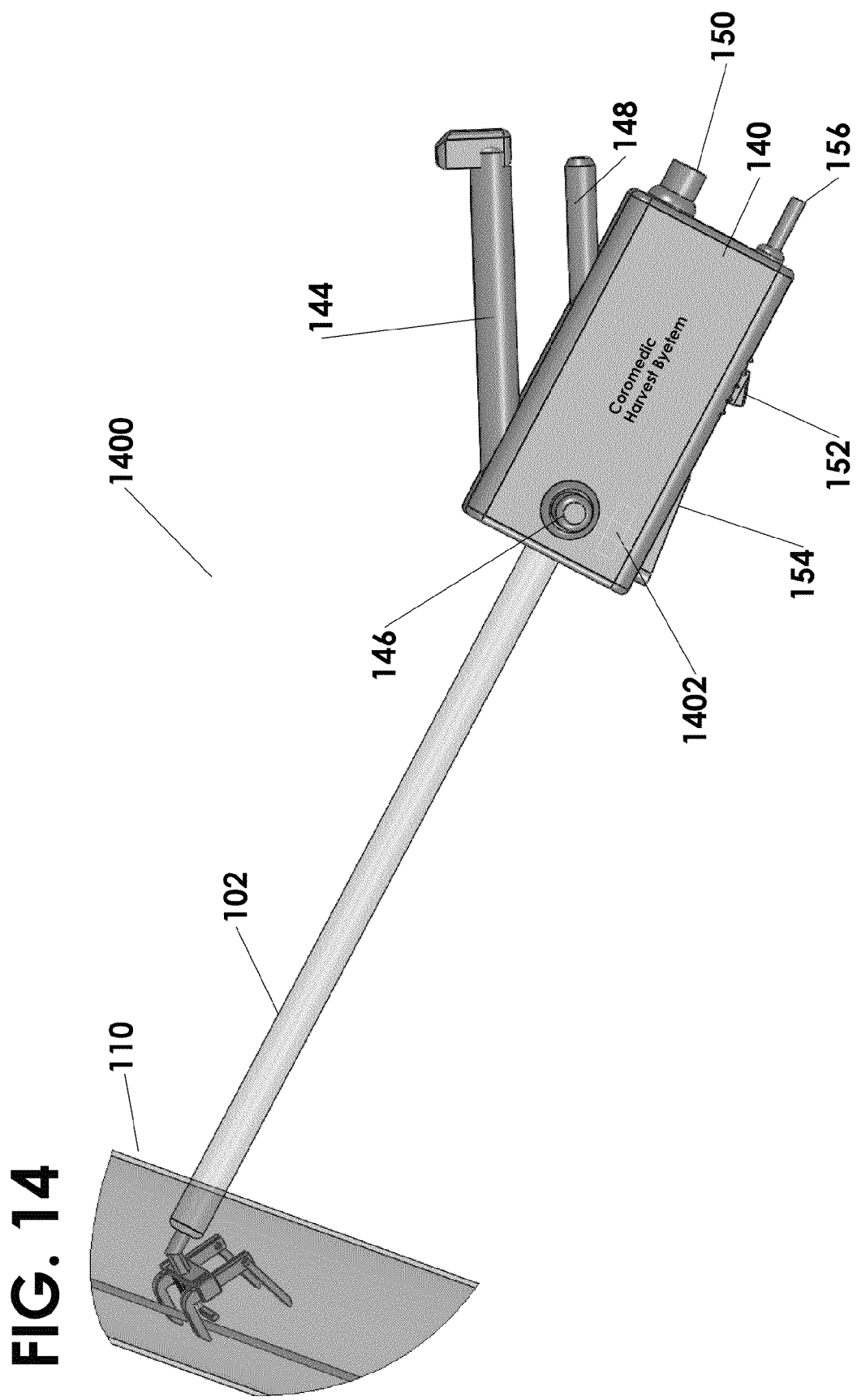
FIG. 14 shows another exemplary, illustrative, non-limiting 25 embodiment of the harvester.

FIG. 14 shows another embodiment of the device of FIG. 1, shown as a harvesting device 1400 featuring a dissector controller 1402 in the form of a joystick as shown. This joystick is actually a second joystick for harvesting device 1400 and preferably separately controls the motion of the dissector head 110.

Figure 15:
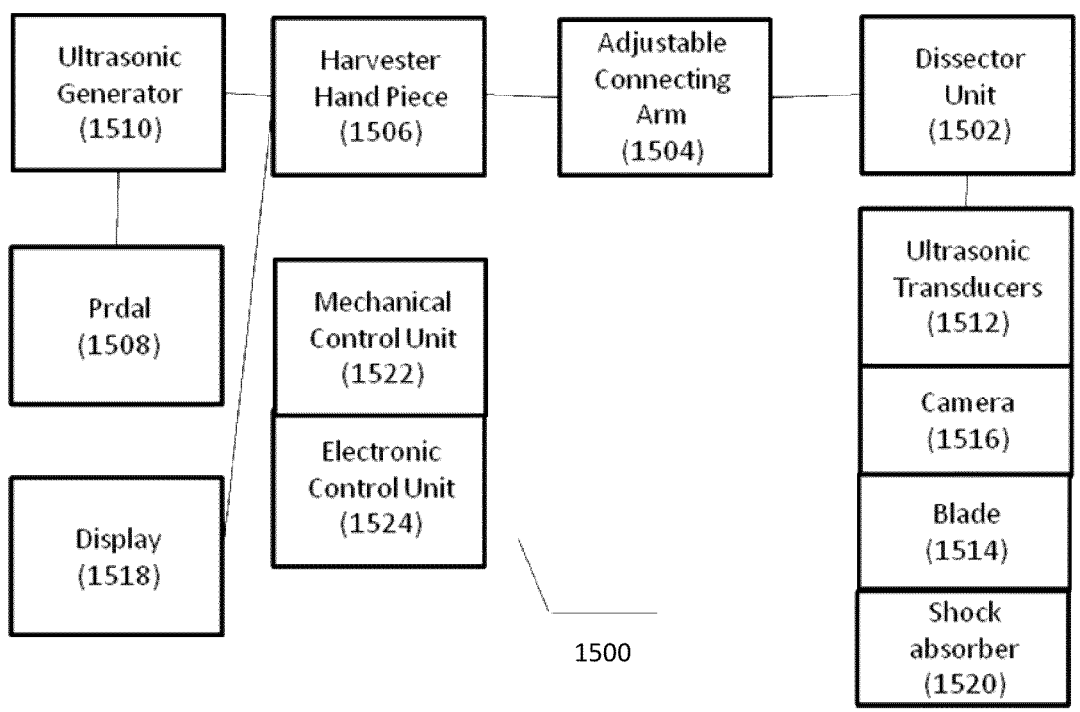
FIG. 15 is a schematic block diagram of an exemplary, illustrative, non-limiting embodiment of a system according to the present invention.

FIG. 15 is a schematic block diagram of an exemplary, illustrative, non-limiting embodiment of a system according to the present invention. As shown, a system 1500 features a dissector unit 1502, which may optionally and preferably be implemented according to any of the embodiments of the dissector head as described herein. Dissector unit 1502 is controllably connected to an adjustable connecting arm 1504 and is preferably controlled by the user through a harvester hand piece 1506. Optionally and more preferably, further control is provided by a foot pedal 1508 or other separate control for controlling functionality of ultrasonic generator 1510.

Dissector unit 1502 preferably features one or more ultrasonic transducers 1512, for which power is provided by ultrasonic generator 1510. Each ultrasonic transducer 1512 preferably provides ultrasonic power to one or more ultrasonic scalpel blades 1514. Such an implementation, in which ultrasonic transducer 1512 is located very close to ultrasonic scalpel blade(s) 1514, is preferred for minimally invasive surgery, as it permits a small, compact dissector unit 1502 to provide power at the location needed. An ultrasonic shock absorber 1520 is also preferably provided in order to absorb any energy from ultrasonic blades 1514.

Dissector unit 1502 also optionally and preferably features a mechanical control unit 1540 for providing mechanical control of the jaws (not shown).

A camera 1516 preferably provides images or other visual information to a display 1518, which may optionally be a computer monitor, television screen or video screen, or any other type of display.

Harvester hand piece 1506 also preferably includes a mechanical control unit 1522, which preferably also controls movements of dissector unit 1502, more preferably including movements of the jaws (not shown) featuring ultrasonic scalpel blade(s) 1514. Harvester hand piece 1506 also preferably includes an electronic control unit 1524, for providing electronic control to dissector unit 1502 (for example for controlling the motor for the pusher (not shown), controlling functionality of ultrasonic scalpel blade(s) 1514 and so forth).

Figure 16:
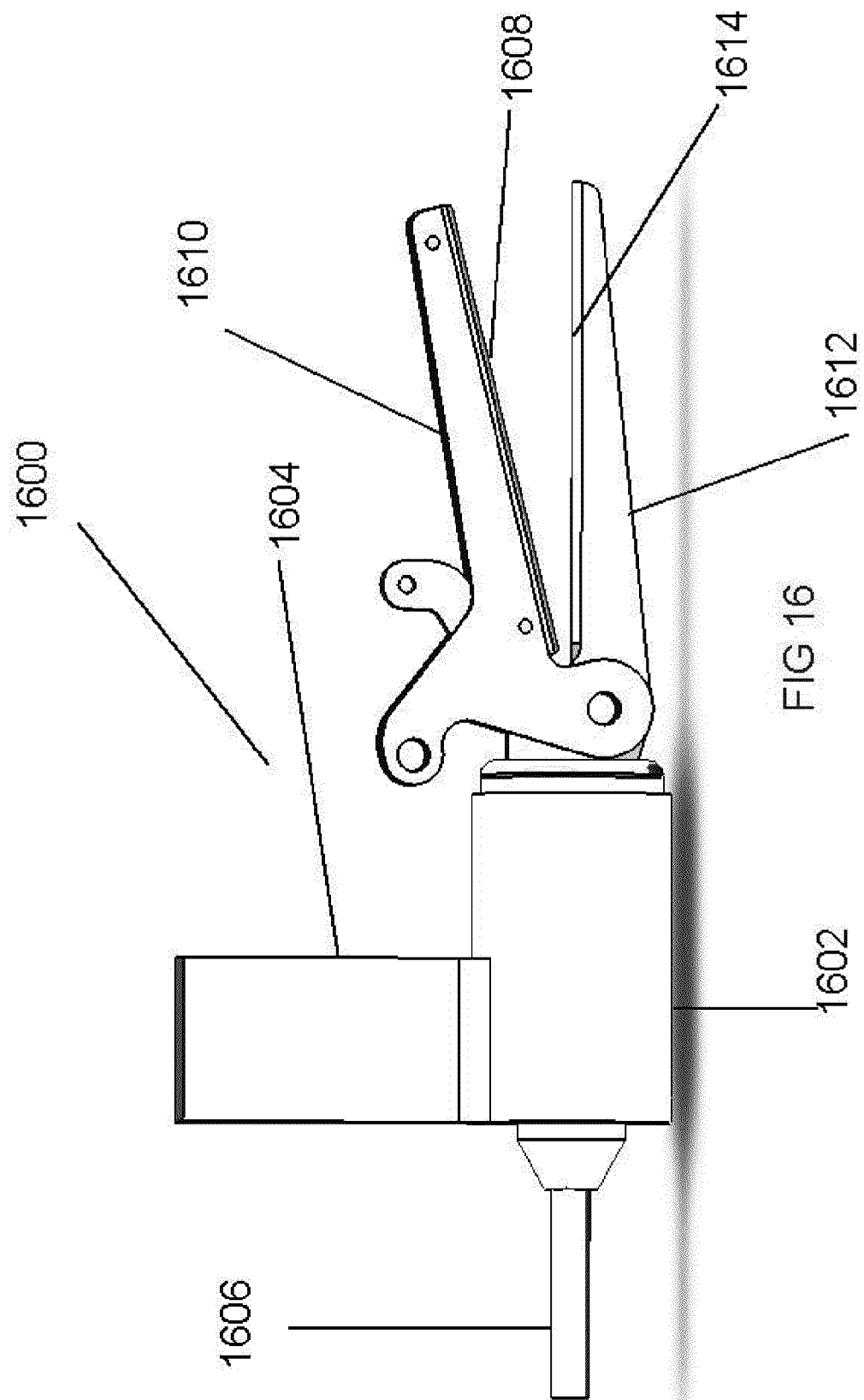
FIG. 16 shows an external view of a portion of the system of FIG. 15.

FIG. 16 shows an external view of a portion of the system of FIG. 15. As shown, a dissector unit 1600 (which may for example optionally be implemented as shown in FIG. 15) preferably features an ultrasound unit 1602, for containing the ultrasonic transducer(s) and any electronics required thereof. Ultrasound unit 1602 is connected for transmitting ultrasonic energy to at least one ultrasonic scalpel blade 1614.

Optionally, a gripping arm 1608 holds the tissue with sufficient tension for the operation of ultrasonic scalpel blade 1614.

A mechanical unit 1604 preferably includes all of the mechanical controls, for example for controlling the movements of upper jaw 1610 and lower jaw 1612.

Ultrasound unit 1602 is also preferably connected to an arm 1606, as is also shown in the other embodiments provided herein and as previously described.

While the invention has been described with respect to a limited number of embodiments, it will be appreciated that many variations, modifications and other applications of the invention may be made.

What is claimed is:

1. A tissue dissecting device adapted for harvesting of a blood vessel, comprising:
   a dissector unit, comprising:
      first and second pairs of jaws, each of the first and second pairs of jaws including a jaw base having first and second end portions, a superior jaw, a pivot pin, and an inferior jaw, the superior jaw being attached to the first end portion of the jaw base, the pivot pin pivotably connecting the inferior jaw to the second end portion of the jaw base, and at least one of the superior jaw and the inferior jaw comprises at least one ultrasonic blade or at least one electrocautery blade and wherein a relative placement of the first and second pairs of jaws is adapted for dissection of a blood vessel,
      an arm having an end portion,
      a bridge connecting the first and second pairs of jaws, the bridge including a horizontal adjustment mechanism configured to control the distance between the first and second pairs of jaws according to a size of a pedicle from the dissection, and
      at least one moveable joint moveably connecting the bridge to the end portion of the arm such that the first and second pairs of jaws have at least two degrees of freedom with respect to the arm, and
      at least one manual operator handle configured to pivot the inferior jaw relative to the jaw base;
   a controller operatively connected to the dissector unit for controlling operation of the at least one ultrasonic blade or the at least one electrocautery blade.

2. The device of claim 1, wherein said at least one ultrasonic blade oscillates at a rate of from about 45 KHz to about 500 KHz.

3. The device of claim 1, wherein said size of said pedicle is from about 5 mm to about 5 cm.

4. The device of claim 3, wherein said size of said pedicle is from about 1 cm to about 4 cm.

5. The device of claim 1, wherein the horizontal adjustment mechanism is configured to control the distance between the first and second pairs of jaws from about 2 mm to about 5 cm.

6. The device of claim 5, wherein the horizontal adjustment mechanism is configured to control the distance between the first and second pairs of jaws from about 1.5 cm to about 3.5 cm.

7. The device of claim 1, wherein only the superior jaw comprises said at least one ultrasonic blade and wherein the inferior jaw holds the blood vessel against the superior jaw for dissection.

8. The device of claim 1, wherein each of the superior and inferior jaws includes an ultrasonic blade.

9. The device of claim 1, wherein the dissector unit includes a dissector head having the first and second pairs of jaws and the bridge, further comprising at least one ultrasonic transducer, wherein said at least one ultrasonic transducer is located in said dissector head.

10. The device of claim 9, wherein said ultrasonic transducer comprises a piezoelectric transducer.

11. The device of claim 10, further comprising an ultrasound generator for generating ultrasonic energy for delivery to said ultrasonic transducer.

12. The device of claim 1, wherein at least one of the superior and inferior jaws is pivotable at an angle of from about 90 degrees to about 120 degrees.

13. The device of claim 1, wherein the superior jaw is fixedly attached to the first end portion of the jaw base.

14. The device of claim 1, wherein the superior jaw is pivotably attached to the first end portion of the jaw base.

* * * * *